United States Patent
Watanabe et al.

(10) Patent No.: US 10,531,684 B2
(45) Date of Patent: Jan. 14, 2020

(54) POWDER CONTAINING FERRIC PYROPHOSPHATE AND METHOD FOR PRODUCING SAME

(71) Applicant: TOMITA PHARMACEUTICAL CO., LTD, Naruto-shi, Tokushima (JP)

(72) Inventors: Sadayoshi Watanabe, Naruto (JP); Yukinori Konishi, Naruto (JP); Shota Minami, Naruto (JP); Akihito Bando, Naruto (JP); Naoyuki Kitamura, Naruto (JP)

(73) Assignee: TOMITA PHARMACEUTICAL CO., LTD., Naruto-shi (JP)

(*) Notice: Subject to any disclaimer, the term of this patent is extended or adjusted under 35 U.S.C. 154(b) by 223 days.

(21) Appl. No.: 15/566,151

(22) PCT Filed: Dec. 10, 2015

(86) PCT No.: PCT/JP2015/084696
§ 371 (c)(1),
(2) Date: Apr. 17, 2018

(87) PCT Pub. No.: WO2016/166920
PCT Pub. Date: Oct. 20, 2016

(65) Prior Publication Data
US 2018/0249750 A1 Sep. 6, 2018

Related U.S. Application Data

(63) Continuation of application No. PCT/JP2015/084696, filed on Dec. 10, 2015.

(30) Foreign Application Priority Data

Apr. 13, 2015 (JP) .................. 2015-82106

(51) Int. Cl.
*A23L 33/16* (2016.01)
*C01B 25/42* (2006.01)
*A61K 33/26* (2006.01)
*A61K 9/14* (2006.01)
*A61K 47/02* (2006.01)

(52) U.S. Cl.
CPC ............. *A23L 33/16* (2016.08); *A61K 9/14* (2013.01); *A61K 33/26* (2013.01); *A61K 47/02* (2013.01); *C01B 25/42* (2013.01); *A23V 2002/00* (2013.01); *A23V 2200/30* (2013.01); *A23V 2250/1578* (2013.01); *A23V 2250/1592* (2013.01); *C01P 2006/12* (2013.01); *C01P 2006/16* (2013.01); *C01P 2006/64* (2013.01)

(58) Field of Classification Search
CPC ......... A23L 33/16; C01B 25/42; A61K 33/26; A61K 9/14; A61K 47/02; C01P 2006/64; C01P 2006/12; C01P 2006/16; A23V 2250/1592; A23V 2250/1578; A23V 2200/30; A23V 2002/00
See application file for complete search history.

(56) References Cited

FOREIGN PATENT DOCUMENTS

| CN | 1415311 | * | 5/2003 | ............ A61P 7/06 |
| KR | 20060040659 | * | 5/2006 | ............ A23L 1/304 |

OTHER PUBLICATIONS

English Translation of CN1415311 (Machine), translated 2019. (Year: 2019).*
English Translation of KR 20060040659 (Machine), translated 2019. (Year: 2019).*

* cited by examiner

Primary Examiner — Trevor Love
(74) Attorney, Agent, or Firm — Locke Lord LLP

(57) ABSTRACT

Provided is a powder containing ferric pyrophosphate that affords high iron absorbability, as a main component of an oral iron preparation. The present invention relates to a composite powder containing ferric pyrophosphate, which is a powder containing ferric pyrophosphate and a sodium component, wherein (1) the content of ferric pyrophosphate is 95 wt % or higher, and (2) a (Fe+Na)/P molar ratio is 0.8 to 1.0.

10 Claims, No Drawings

POWDER CONTAINING FERRIC PYROPHOSPHATE AND METHOD FOR PRODUCING SAME

CROSS-REFERENCE TO RELATED APPLICATIONS

The present application claims the benefit of International Application No. PCT/JP2015/084696, filed on Dec. 10, 2015, which claims priority to Japanese Application No. 2015-082106 filed Apr. 13, 2015, the disclosures of which are incorporated herein by reference.

TECHNICAL FIELD

The present invention relates to a powder containing ferric pyrophosphate, used for instance in iron supplementation foodstuffs for the purpose of orally supplementing iron into the body, and relates to a method for producing the same.

BACKGROUND ART

Insufficient intake of minerals has been pointed out in recent years as one cause pertaining to disease prevention and health maintenance of the human body. In this context, there is ongoing research and analysis devoted to elucidating the roles of various minerals. Among these minerals, about 70% of iron in the human body is present in heme iron of oxygen-transporting hemoglobin. When iron is insufficient, the amount of hemoglobin decreases and oxygen carrying capacity decreases accordingly, whereupon anemia develops. Iron deficiency such as anemia affect about 2 billion people in the entire population. Iron deficiency is found to give rise not only to the onset of anemia but also, among others, to the birth of low-weight infants from pregnant women, as well as to abnormal behavior and developmental delays in children. Oral supplementation of iron is a known treatment method for such diseases.

Internal absorption of orally ingested iron takes place in the form of absorption of divalent iron ions ($Fe^{2+}$) in the duodenum. Foodstuffs and drugs for alleviating or healing iron deficiency disorders have been developed with the above mechanism in mind. For instance, products are provided in which iron preparations are blended into soft drinks, powdered milk, supplements, drugs and the like. Iron preparations that are used include preparations having soluble iron salts or water-insoluble iron salts as a main component, with soluble salts being widely used in particular. However, soluble iron salts have a strong iron taste, and thus are problematic, in oral use from the viewpoint of palatability. Moreover, soluble iron salts have problematic side effects derived from intrusion of ionized iron into the stomach wall. In consequence, insoluble iron salts have come to be used in recent years, with ferric pyrophosphate drawing substantial attention among such insoluble iron salts.

The iron dissolving effect in the stomach and the duodenum has a bearing on iron absorbability. If it were possible to increase dissolving of iron in the duodenum, through decrease of dissolving in the stomach, then bioabsorbability could be conceivably enhanced thanks to the resulting increase in dissolving at the duodenum. In contrast to soluble iron salts, moreover, it is found that insoluble iron salts allow alleviating or preventing the problem of stomach invasion. On the other hand, insoluble iron salts such as ferric pyrophosphate have poor iron solubility and exhibit accordingly low bioabsorbability, despite being comparatively little prone to causing disorders in the stomach. In order to solve these problems, chelate iron formulations have been developed in which for instance ferric pyrophosphate is solubilized. However, the occurrence of iron dissolving in the stomach might be a cause of vomiting, diarrhea and anorexia. Accordingly, various improved technologies have been proposed which pertain to iron preparations that contain ferric pyrophosphate.

As one such iron preparation, a ferric pyrophosphate formulation has been proposed in which microparticles of ferric pyrophosphate are prepared through addition of a dispersant to ferric pyrophosphate used for instance as a food additive; as a result, dispersibility is enhanced, and the flavor of iron is reduced thereby (Patent Document 1).

Also known are iron-reinforced milk beverages in which secondary aggregation during storage is prevented effectively through addition of sodium caseinate to microparticulate ferric pyrophosphate (Patent Document 2).

Soluble ferric pyrophosphate has also been proposed embodied in the form of a mixture resulting from blending sodium pyrophosphate, sodium citrate and the like, in order to increase the solubility of ferric pyrophosphate (Patent Document 3, paragraph [0016]).

Other research works pertaining to the bioabsorbability of ferric pyrophosphate have been reported in the literature. These include for instance evaluation of the bioabsorbability of ferric pyrophosphate with modified loss on ignition (Non-patent Document 1), evaluation of the bioabsorbability of ferric pyrophosphate with a modified average particle size (Non-patent Document 2), and evaluation of the bioabsorbability of soluble ferric pyrophosphate (Non-patent Document 3).

CITATION LIST

Patent Document

[Patent Document 1] Japanese Patent Application No. H08-514448
[Patent Document 2] Japanese Patent Application Publication No. 2012-100615
[Patent Document 3] Japanese Patent Application Publication No. 2009-108027

Non-Patent Document

[Non-patent Document 1] H. Tsuchita, et al., J. Argric. Food Chem., 39, 316-321 (1991)
[Non-patent Document 2] R. Wegmuller, et al., J. Nutr., 134, 3301-3304 (2004)
[Non-patent Document 3] L. Zhu, et al., J. Argric. Food Chem., 57, 5014-5019 (2009)

SUMMARY OF INVENTION

Technical Problem

In the technique of Patent Documents 1 and 2, however, the compounding amount of ferric pyrophosphate contained in the food additive formulations is small, and accordingly the food additive formulations have to be taken in significant amounts for iron ingestion. Further, grinding using a bead mill or the like is resorted to in order to obtain microparticles, which entails accordingly a higher risk of contamination from beads or from the equipment.

In Non-patent Document 1, the bioabsorbability of ferric pyrophosphate rises with increasing an ignition loss of the ferric pyrophosphate, but remains nevertheless insufficient. The bioabsorbability of ferric pyrophosphate in Non-patent Document 2 increases with decreasing the average particle size, but still no dramatic improvement in bioabsorbability is achieved. The evaluation of bioabsorbability in Non-patent Document 3, using cells, reveals higher bioabsorbability than those of other water-soluble iron salts, but actual ingestion is accompanied by an iron taste that may upset the stomach.

The soluble ferric pyrophosphate disclosed in Patent Document 3 is chelated using an organic acid such as citric acid; as a result, normal solubility is increased. However, there remains room for improvement as regards iron absorbability by the human body. Specifically, iron is absorbed in humans mainly through the duodenum. When most of an iron preparation dissolves in the stomach, however, the stomach may be upset and in consequence iron ions may react with contaminants in the stomach to form insoluble iron salts. The insoluble iron salts cannot be absorbed effectively in the duodenum. As a result, sufficient iron absorbability may fail to be achieved. Soluble ferric pyrophosphate as well should therefore be improved in terms of iron absorbability by the human body.

Accordingly, a main object of the present invention is to provide a ferric pyrophosphate-containing powder that affords high iron absorbability, as a main component of an oral iron-containing agent.

Solution to Problem

As a result of diligent research conducted in the light of conventional problems, the inventors found that the above goal can be attained by a ferric pyrophosphate-containing powder having a specific composition, and perfected the present invention on the basis of that finding.

Specifically, the present invention is a powder containing ferric pyrophosphate, and a method for producing that powder, as follows.

1. A composite powder containing ferric pyrophosphate, which is a powder containing ferric pyrophosphate and a sodium component, wherein (1) the content of ferric pyrophosphate is 95 wt % or higher, and (2) a (Fe+Na)/P molar ratio is 0.8 to 1.0.

2. The composite powder containing ferric pyrophosphate according to 1, having a mode diameter (pore diameter of the maximum frequency) of 500 nm or less.

3. The composite powder containing ferric pyrophosphate according to 1, having a hue, the b value of which, in the CIE LAB color system, is 16 or smaller.

4. The composite powder containing ferric pyrophosphate according to 1, containing 0.5 to 4.5 wt % of Na.

5. The composite powder containing ferric pyrophosphate according to 1, containing 1 to 4.5 wt % of Na.

6. The composite powder containing ferric pyrophosphate according to 1, having a specific surface area of 15 $m^2/g$ or higher.

7. An iron supplement foodstuff, containing the composite powder according to any one of 1 to 5.

8. A pharmaceutical composition, containing the composite powder according to any one of 1 to 5.

9. A method for producing a composite powder containing ferric pyrophosphate, the composite powder containing ferric pyrophosphate and a sodium component, the method including:

a step of preparing an aqueous slurry that contains a reaction product obtained by reacting a water-soluble ferric salt, a pyrophosphate and a carbonate in an aqueous solvent, the aqueous slurry being prepared through addition and mixing such that a (Fe+Na)/P molar ratio of the reaction product is 0.8 to 1.0.

10. The production method according to 8, wherein the carbonate is sodium carbonate.

11. The production method according to 8, wherein a water-soluble iron salt, a pyrophosphate and a carbonate, which are prepared in the form of aqueous solutions beforehand, are added and mixed such that a molar ratio (Fe+Na)/P of the starting material charge is 2.7 to 3.1.

Advantages of Invention

The powder of the present invention is a composite powder in which in particular a (Fe+Na)/P molar ratio is controlled to lie in the range of 0.8 to 1.0. In connection with iron dissolution or solubility, it becomes accordingly possible to reduce iron dissolution or solubility in water at pH 1.2 while increasing solubility in water at pH 3.0. That is, high absorbability can be expected to be achieved by virtue of the fact that iron dissolution or solubility is higher in the duodenum than in the stomach, while there is effectively reduced dissolving of iron ions in the stomach, upon oral ingestion of the powder of the present invention. As a result an oral powder can be provided that allows iron to be absorbed more readily by the body, with little stomach upsetting.

The powder of the present invention having such features, can be taken or be administered orally as-is, and can also be used blended with various products such as foodstuffs, supplements, drugs and quasi-drugs.

By prescribing in particular a predetermined amount of a carbonate to be present in the reaction system, furthermore, the production method of the present invention allows producing more reliably and efficiently the powder of the present invention in which a specific amount of sodium is composited with ferric pyrophosphate.

DESCRIPTION OF EMBODIMENTS

1. Ferric Pyrophosphate-Containing Composite Powder

The composite powder of the present invention (powder of the present invention) is a powder containing ferric pyrophosphate and a sodium component, wherein (1) the content of ferric pyrophosphate is 95 wt % or higher, and (2) a (Fe+Na)/P molar ratio is 0.8 to 1.0.

Generally ferric pyrophosphate is a compound represented by chemical formula $Fe_4(P_2O_7)_3$, but the compound referred to as soluble ferric pyrophosphate has no definite chemical formula, and is known as a mixture of ferric pyrophosphate, sodium pyrophosphate, sodium citrate and the like. The dissolution properties of these sodium compounds themselves are reflected on ferric pyrophosphate, which exhibits thus high solubility in water, and nearly all sodium dissolves in it. In contrast, the powder of the present invention is composed of a component in which ferric pyrophosphate and a specific amount of sodium are composited (integrally immobilized) with each other. Accordingly, the dissolving volume of sodium in the powder of the present invention with respect to water is very low, ordinarily of 0.30 mg/mL or less (90° C.), in particular 0.20 mg/mL or less (90° C.). Therefore, the powder of the present invention can be clearly distinguished from mixtures such as those above.

In the powder of the present invention the individual particles that make up the powder contain a component resulting from compositing ferric pyrophosphate and a specific amount of sodium. Such a powder can be produced yet more reliably in accordance with a production method such as the one described below.

The above component being a composite of ferric pyrophosphate and a sodium component is ordinarily an amorphous material. Therefore, for example, clear peaks of the sodium compound cannot be observed by X-ray diffraction analysis.

The content of ferric pyrophosphate in the powder of the present invention is usually 95 wt % or higher, particularly preferably 98 wt % or higher. The upper limit value of the content of ferric pyrophosphate is not limited, but may be ordinarily set to about 99 wt %.

In terms of the above compositing, the sodium contained in the powder of the present invention is preferably derived from a starting material (sodium source) during the production of the powder of the present invention. The above content can be adjusted as appropriate for instance in accordance with the type of starting material that is used, but in particular the (Fe+Na)/P molar ratio is set to about 0.8 to 1.0, preferably 0.82 to 0.99. When the molar ratio is lower than 0.8, the dissolution or solubility of iron in water at pH 3.0 is low, and accordingly iron dissolution or solubility in the duodenum is low. When the molar ratio exceeds 1.0, the dissolution or solubility in water at pH 1.2 is high, and accordingly the content of ferric pyrophosphate in the powder that reaches the duodenum is small, and the dissolving volume of iron in the duodenum is likewise small.

The content of sodium in the powder of the present invention is not limited, so long as the above molar ratio is satisfied, but is generally 0.5 to 4.5 wt %, and is set in particular to about 1 to 4.5 wt %, preferably 1 to 4 wt %. Yet higher iron absorbability can be achieved by setting such ranges.

As to a form, the powder of the present invention can adopt ordinarily the form of a powder (dry powder). In this case, the average particle diameter is not limited, and may be usually set to about 1 to 100 μm, in particular 1 to 50 μm. The powder of the present invention can be used, as needed, in the form of a liquid such as a dispersion or a paste, by being dispersed in a liquid medium containing water or the like. In connection with the average particle diameter, a sample was subjected to ultrasonic agitation (ultrasonic output 40 W) for 3 minutes, was thereafter dispersed in water, and the average particle diameter in the water solvent was measured by laser diffraction. The measured values are obtained using "Microtrac MT3300EX II" by MicrotracBEL Corp.

The specific surface area of the powder of the present invention is not limited, but is usually 10 $m^2$/g or higher, and more preferably is set, in particular, to 15 $m^2$/g or higher, from the standpoint of the advantages of the present invention. The mode diameter (pore diameter of the maximum frequency) of the pores of the powder (particles) of the present invention is not limited, but is ordinarily 600 nm or less, and is more preferably set to 500 nm or less, from the viewpoint of the effect of the present invention.

The hue of the powder of the present invention is generally white. From the point of view that the powder is blended into foodstuffs, drugs or the like, the b value of the powder is preferably 16.5 or less, and particularly preferably 16 or less, in the CIE LAB color system representing yellow to blue. That is, the powder of the present invention is preferably not yellowish but white or near white.

The powder of the present invention can be suitably used orally. Therefore, the powder of the present invention can be used, as-is, in the form of an oral iron-containing agent (for iron supplementation), and also in the form of a formulation for iron supplement resulting from formulating the powder of the present invention with other components (additives such as solvents, thickeners, excipients, coloring agents and flavorings). The powder of the present invention can be used as an auxiliary component in ordinary foodstuffs, supplements, drugs and the like.

2. Method for Producing a Powder Containing Ferric Pyrophosphate

The present invention encompasses a method for producing a composite powder containing ferric pyrophosphate and a sodium component, the method including:

a step (reaction step) of preparing an aqueous slurry that contains a reaction product obtained by reacting a water-soluble ferric salt, a pyrophosphate and a carbonate in an aqueous solvent, the aqueous slurry being prepared through addition and mixing such that a (Fe+Na)/P molar ratio of the reaction product is 0.8 to 1.0.

Reaction Step

In the reaction step there is prepared an aqueous slurry that contains a reaction product obtained by reacting a water-soluble ferric salt, a pyrophosphate and a carbonate in an aqueous solvent, the aqueous slurry being prepared through addition and mixing such that a (Fe+Na)/P molar ratio of the reaction product is 0.8 to 1.0.

The water-soluble iron salt is not particularly limited, and examples thereof include ferric chloride, ferric sulfate, ferric ammonium sulfate, ferric nitrate, ferric bromide, ferric formate, ferric acetate, ferric citrate and ferric ammonium sulfate. Preferred among the foregoing are at least one from among ferric chloride, ferric sulfate, ferric nitrate and the like, and more preferably at least one from among ferric chloride and ferric sulfate, most preferably ferric chloride.

The pyrophosphate is not particularly limited, and examples thereof include sodium pyrophosphate, potassium pyrophosphate, lithium pyrophosphate, acidic sodium pyrophosphate and acidic potassium pyrophosphate. Particularly preferred among the foregoing are at least one from among sodium pyrophosphate, potassium pyrophosphate, acidic sodium pyrophosphate and the like, yet more preferably at least one from among sodium pyrophosphate and potassium pyrophosphate, most preferably sodium pyrophosphate.

The carbonate is not particularly limited, and examples thereof include sodium carbonate, sodium hydrogen carbonate, potassium carbonate, potassium hydrogen carbonate, lithium carbonate and lithium hydrogen carbonate. Preferred among the foregoing are at least one from among sodium carbonate, sodium hydrogen carbonate, potassium carbonate, potassium hydrogen carbonate and the like, particularly preferably at least one from among sodium carbonate and potassium carbonate, most preferably sodium carbonate.

The production method of the present invention involves addition and mixing of an aqueous solution of an iron salt, a pyrophosphate and a carbonate in such a manner that the reaction product has a (Fe+Na)/P molar ratio of 0.8 to 1.0. Accordingly, in particular a sodium salt is used as at least one of the above pyrophosphate and carbonate. In the present invention, a carbonate is used particularly preferably as the sodium source.

At least one from among water and a water-soluble organic solvent can be suitably used as the aqueous medium. As the water-soluble organic solvent there can be preferably used an alcohol such as methanol, ethanol or propanol. Water is used particularly preferably in the present invention. The use amount of the aqueous medium is not particularly limited, and may be set so that the solids concentration of the reaction product is ordinarily 0.1 to 40 wt %, more preferably about 0.3 to 50 wt %.

The production method of the present invention may be a method that involves adding the aqueous solution iron salt, the pyrophosphate and the carbonate to the aqueous medium; alternatively, aqueous solutions of the foregoing may be prepared beforehand and be then added and mixed together. The concentration of the respective aqueous solutions is not particularly limited, and it suffices to ordinarily prescribe the aqueous solution iron salt to lie in the range of about 1 to 2 mol/L, the pyrophosphate in the range of about 0.1 to 1 mol/L and the carbonate in the range of about 0.01 to 0.15 mol/L.

If necessary, a pH regulator or the like may be added to the aqueous medium of the present invention. Examples of pH regulators that can be used include hydrofluoric acid, hydrochloric acid, hydrobromic acid, hydriodic acid, sulfuric acid, nitric acid, phosphoric acid, acetic acid, citric acid, oxalic acid, aluminum chloride, lithium hydroxide, sodium hydroxide, potassium hydroxide and aqueous ammonia.

An aqueous slurry containing the desired reaction product can be obtained in the production method of the present invention by mixing the starting materials, weighed so as to yield predetermined proportions, in the aqueous medium, and allowing the starting materials to react. Preferably, the charge amounts of the starting materials are set in such a manner that for instance the (Fe+Na)/P molar ratio lies in the range of 2.7 to 3.1. The desired powder containing ferric pyrophosphate can be prepared as a result more reliably.

The reaction temperature is not particularly limited, and may be set as appropriate to for instance 5° C. to 50° C., and in particular so as to lie in the range of 15° C. to 35° C. The reaction atmosphere is not particularly limited, and may be the atmosphere (atmospheric pressure).

The pH in the reaction system at the time of the reaction (during the reaction) is not particularly limited, and is set ordinarily to about 1.0 to 5.0, particularly preferably to 1.5 to 3.0, and yet more preferably to 1.6 to 2.2, from the viewpoint of allowing the particle size to be controlled. In the production method of the present invention, the pH of the aqueous slurry containing the reaction product after addition of all the starting materials is preferably adjusted so as to lie in the range of 2.0 to 5.0, from the viewpoint of reducing the generation of by-products such as iron hydroxide. Herein, the pH above may be adjusted by employing, in addition to a method for adjusting the addition rates of the various starting materials, a method that involves adding a known pH regulator (for example, hydrofluoric acid, hydrochloric acid, hydrobromic acid, hydriodic acid, sulfuric acid, nitric acid, phosphoric acid, acetic acid, citric acid, oxalic acid, aluminum chloride, lithium hydroxide, sodium hydroxide, potassium hydroxide or aqueous ammonia).

An aqueous slurry containing the reaction product is thus obtained, but an aging step may be further carried out as needed. The aging step may be accomplished through continued stirring, a mixed solution once addition of all the starting materials is complete for a given lapse of time. As a result, the production reaction of ferric pyrophosphate can be promoted. The temperature in the aging step may be ordinarily set to about 5° C. to 80° C., and particularly preferably 10° C. to 50° C. The aging time may be set to last for about 0.15 to 5 hours, and particularly preferably 0.15 to 1 hour, immediately following complete addition of all the starting materials.

The solids concentration of the aqueous slurry in the aging step is not particularly limited, and is ordinarily set to about 1 to 20 wt %, particularly preferably to 3 to 15 wt %. Water may be removed or added as appropriate in order to adjust the solids concentration.

Other Steps

The aqueous slurry is ordinarily a liquid in which there is dispersed the powder of the present invention, being the reaction product; the aqueous slurry can therefore be used as-is. If necessary, the aqueous slurry may also be subjected to any step from among a solid-liquid separation step, a water washing step, a drying step, a grinding/classification step or the like.

Solid-Liquid Separation Step

In the solid-liquid separation step solids are recovered through solid-liquid separation of the aqueous slurry. Any known dewatering method, for instance filtration or centrifugation may be used as the solid-liquid separation method.

Water Washing Step

A water washing step can be performed as appropriate on the aqueous slurry, as a pre-process and/or post-process of the solid-liquid separation step. The water washing step allows removing more effectively any by-products, impurities and the like that the reaction product may contain.

More preferably, the water washing step can be repeated alternately with the solid-liquid separation step. Therefore, the water washing step may involve performing once, twice or more times a series of steps that include for instance dewatering of the aqueous slurry in accordance with an ordinary filtration method such as pressure filtration, reduced-pressure filtration, vacuum filtration, natural filtration or centrifugal filtration, and washing then with water the obtained solids, using ordinary water washing equipment, followed by solid-liquid separation using for instance a filter press or a centrifuge.

The end point of the water washing step is not limited, and may be for instance set to an electric conductivity (22° C.) of 100 to 200 μS/cm, more preferably of 100 to 150 μS/cm, of the washing filtrate, in a case where for instance a filter press is used.

Drying Step

The solids after solid-liquid separation or after the water washing step can be subjected to a drying step as needed. The drying temperature may be set as appropriate to lie in the range of 20° C. to 400° C.; herein drying is preferably carried out in particular at 80° C. to 120° C. The drying time can be set as appropriate depending on the drying temperature; preferably, the drying time is set so that loss on ignition is 30% or less, particularly preferably 20% or less.

The drying method is not limited, and for instance drying may be carried out by resorting to an ordinary method such as warm air drying, infrared drying, hot plate drying, vacuum drying, suction drying and steam drying, hot pure water-lift drying, Marangoni drying, air knife draining, spin drying and roll drying with "draining". Ordinary drying equipment such as stationary shelve/box dryers, spray dryers, band dryers, vacuum dryers, freeze dryers, microwave dryers, drum dryers and fluidized dryers can be used herein.

Grinding Step

The generated powder of the present invention can be ground as needed. An ordinary method such as dry grinding, wet grinding and freeze grinding can be used herein as the grinding method. The grinding equipment that can be used includes general equipment such as, for instance, jet mills, feather mills, hammer mills, pulverizers, ball mills and bead mills. The degree of grinding can be adjusted as appropriate, but ordinarily the average particle size after grinding is set to about 1 to 100 μm, particularly preferably to 1 to 50 μm. The ground material can be classified in order to adjust the material to a desired particle size.

Dispersion Step

In a case where the powder of the present invention is used in the form of a liquid (dispersion), as explained in 1 above, it suffices to utilize the powder of the present invention, or an aqueous slurry thereof, obtained as a result of any one of the solid-liquid separation step, the water washing step, the drying step, the grinding step and the like, to prepare a dispersion by using the powder or the aqueous slurry. Known equipment such as mixers, emulsifiers, wet crushers and planetary ball mills can be used for preparing the dispersion. Various additives may be added as appropriate, apart from dispersants for increasing dispersibility.

EXAMPLES

The features of the present invention will be explained next more specifically by way of examples and comparative examples. The scope of the present invention is however not limited to the examples. In the disclosure of the examples, "%" and "ppm" denote "wt %" and "ppm by weight", respectively.

Example 1

Herein 240 mL of water were measured and poured in a 1 L container, and then a 1.81 mol/L aqueous solution of ferric chloride, a 0.56 mol/L aqueous solution of sodium pyrophosphate and a 0.13 mol/L aqueous solution of sodium carbonate were added to the water so that a molar ratio (Fe+Na)/P of the starting material charge was 2.90, and the whole was stirred at 400 rpm. The addition rate of the various starting materials was adjusted herein so that the pH of the reaction system was 1.6 to 1.7. Once addition was over, the reaction system was aged through stirring for 10 minutes at room temperature, to yield an aqueous slurry containing a reaction product. The final pH after aging was over was 3.6. After aging, the aqueous slurry was dewatered through filtration, and was washed with water. The obtained reaction product was placed in a dryer, with drying at 105° C. for 16 hours, and the dried product was ground in a desk mill, to yield Sample 1.

Example 2

Sample 2 was obtained in the same way as in Example 1, but herein the aqueous solution of sodium carbonate was set to 0.19 mol/L, with adjustment such that the molar ratio (Fe+Na)/P of the starting material charge was 3.02. The final pH after aging was over was 4.5.

Example 3

Sample 3 was obtained in the same way as in Example 1, but herein the aqueous solution of sodium carbonate was set to 0.06 mol/L, with adjustment such that the molar ratio (Fe+Na)/P of the starting material charge was 2.78. The final pH after aging was over was 2.4.

Example 4

Sample 4 was obtained in the same way as in Example 1, but herein the aqueous solution of sodium carbonate was set to 0.04 mol/L, with adjustment such that the molar ratio (Fe+Na)/P of the starting material charge was 2.73. The final pH after aging was over was 2.0.

Example 5

Sample 5 was obtained in the same way as in Example 1, but herein the aqueous solution of sodium carbonate was set to 0.06 mol/L, with adjustment such that the molar ratio (Fe+Na)/P of the starting material charge was 2.78, and with drying for 90 minutes at 700 w in a microwave dryer DR-Y 21, by Twinbird Corporation. The final pH after aging was over was 2.2.

Comparative Example 1

Comparative sample 1 was obtained in the same way as in Example 1, but herein no aqueous solution of sodium carbonate was added, and the whole was adjusted such that the molar ratio (Fe+Na)/P of the starting material charge was 2.67. The final pH after aging was over was 1.7.

Comparative Examples 2 and 3

As Comparative example 2, there was used "Food additive ferric pyrophosphate" (Lot No.: L20816) (Comparative sample 2) by Tomita Pharmaceutical Co., Ltd. As Comparative example 3, there was used "Ferric pyrophosphate" (Lot No.: 408044) (Comparative sample 3) by Yoneyama Chemical Industry Co., Ltd.

Test Example 1

Each sample in the examples and the comparative examples was measured for molar ratios based on iron, phosphorus and sodium contents, b value in the CIE LAB color system, BET specific surface area, mode diameter (pore diameter of the maximum frequency), ferric pyrophosphate content and soluble sodium amount. The results are given in Tables 1 and 2. The measurements were carried out in accordance with the methods below.

(1) Iron Content
<Preparation of a Sample Solution>
Herein 1 g of a sample was weighed precisely in a beaker, then 10 mL of hydrochloric acid (1→2) were added, the sample was dissolved through heating, and the resulting solution was transferred to a volumetric flask, which was then accurately brought to 50 mL with ultrapure water. Then 5 mL of the prepared solution were accurately measured in a volumetric flask and were accurately brought to 100 mL with ultrapure water, to yield a 1000-fold diluted sample solution.
<Preparation of Standard Solutions>
Yttrium standard solution (100 ppm):
Herein 10 mL of an yttrium standard solution (1000 ppm) for atomic absorption analysis and 1 mL of dilute nitric acid were accurately measured in a volumetric flask, and ultrapure water was added to up to 100 mL.
Iron standard solution (100 ppm):
Herein 10 mL of an iron standard solution (1000 ppm) for atomic absorption analysis and 1 mL of dilute nitric acid were accurately measured in a volumetric flask, and ultrapure water was added to up to 100 mL.
Standard addition solution (a) (Fe: 0 ppm):
Herein, 1 mL of an yttrium standard solution (100 ppm), 1 mL of dilute nitric acid, and 1 mL of a 1000-fold diluted solution were accurately measured in a volumetric flask, and ultrapure water was added up to 50 mL.

Standard addition solution (b) (Fe: 2 ppm):

Herein 1 mL of an yttrium standard solution (100 ppm), 1 mL of dilute nitric acid, 1 mL of a 1000-fold diluted solution and 1 mL of an iron standard solution (100 ppm) were accurately measured in a volumetric flask, and ultrapure water was added to 50 mL.

Standard addition solution (c) (Fe: 8 ppm):

Standard addition solution (c) was prepared in the same way as the standard addition solution (b) except that there were accurately measured 4 mL of an iron standard solution (100 ppm) as the standard solution.

<Measurement Method>

Inductively coupled plasma emission spectroscopy (ICP); standard addition method Detection wavelength: 259.941 nm The intensities of standard addition solutions (a), (b) and (c) were measured sequentially, to create a calibration curve. Next, the intensity of standard addition solution (a) was measured, and the iron content per 1 g of the product was calculated in accordance with Expression 1 below.

$$\text{Fe (\%)}=a/\text{collected amount}\times 50\times 1000 \qquad \text{(Expression 1)}$$

(where a=iron concentration (%) in the measurement solution)

ICP: Vista-PRO (Seiko Instruments Inc.)

Iron standard solution for atomic absorption analysis: Wako Pure Chemical Industries, Ltd.

(2) Phosphorus Content

The content of phosphorus was measured according to (1) in Test example 1, but herein a phosphorus standard solution (100 ppm) was used as the standard solution, and the measurement was performed at a detection wavelength of 177.495 nm.

(3) Sodium Content

<Preparation of Standard Solutions>

Sodium standard solution (50 ppm):

Herein 5 mL of a sodium standard solution (1000 ppm) for atomic absorption analysis were accurately measured in a volumetric flask, and ultrapure water was added to up to 100 mL.

Standard addition solution (d) (Na: 0 ppm):

Herein 1 mL of yttrium standard solution (100 ppm) and 5 mL of a 1000-fold diluted solution were accurately measured in a volumetric flask, and ultrapure water was added up to 50 mL.

Standard addition solution (e) (Na: 0.5 ppm):

Herein 1 mL of an yttrium standard solution (100 ppm), 5 mL of a 1000-fold diluted solution and 0.5 mL of a sodium standard solution (50 ppm) were measured accurately in a volumetric flask, and ultrapure water was added up to 50 mL.

Standard addition solution (f) (Na: 5 ppm):

Standard addition solution (f) was prepared in the same way as standard addition solution (e), but herein there were accurately measured 5 mL of the sodium standard solution as the standard solution.

<Measurement Method>

Inductively coupled plasma emission spectroscopy (ICP); standard addition method Detection wavelength: 589.592 nm The intensities of standard addition solutions (d), (e) and (f) were measured sequentially, to create a calibration curve. The intensity of standard addition solution (d) was measured next, and the sodium content per 1 g of the product was calculated in accordance with Expression 2 below.

$$\text{Na (\%)}=b/\text{collected amount}\times 10\times 1000 \qquad \text{(Expression 2)}$$

(where b=sodium concentration (%) in the measurement solution)

ICP: Vista-PRO (Seiko Instruments Inc.)

Sodium standard solution for atomic absorption analysis: Wako Pure Chemical Industries, Ltd.

(4) (Fe+Na)/P Molar Ratio in Powder Containing Ferric Pyrophosphate

The (Fe+Na)/P molar ratio in the powder containing ferric pyrophosphate was calculated, according to Expression 3 below, on the basis of the contents obtained in (1), (2) and (3) of Test example 1.

$$\text{(Fe+Na)/P}=(\text{Fe (\%)}/55.85+\text{Na (\%)}/22.99)/(\text{P (\%)}/30.97) \qquad \text{(Expression 3)}$$

(5) b Value in CIE LAB Color System

Japan's Specifications and Standards for Food Additives include color standards for characterization of ferric pyrophosphate. The standard covers yellow to yellowish-brown colorations. Accordingly, the b value in the CIE LAB color system was measured in order to quantify yellow color numerically. The b value represents yellow to blue. A positive b value denotes yellow whereas a negative b value denotes blue. The greater the absolute value, the stronger is the color denoted thereby. Experiments were therefore carried out in accordance with the method set forth below.

About 0.5 g of a sample were measured in a measurement cell, and the b value in the CIE LAB color system was measured using a "Color meter ZE6000" by Nippon Denshoku Industries Co., Ltd.

(6) Mode Diameter (Pore Diameter of the Maximum Frequency)

Measurements were performed under the conditions below using a mercury porosimeter ("PoreMaster 60GT" by Quantachrome Instruments).

Measurement and analysis: herein 0.05 g of a sample were weighed accurately, were sealed in a measurement cell, and mercury adsorption isotherms from mercury intrusion were worked out to calculate the mode diameter.

(7) BET Specific Surface Area

The BET specific surface area was measured under the operating conditions below, using a high-speed specific surface area pore distribution measuring device ("NOVA-4200e", by Quantachrome Instruments).

Pretreatment: herein 0.8 g of sample were accurately weighed and were sealed in an adsorption pipe that was then degassed for 1 hour at 105° C.

Measurement and analysis: adsorption isotherms of nitrogen gas at the liquid nitrogen gas temperature were worked out, and the specific surface area was calculated in accordance with a multipoint BET method, using the adsorption isotherms.

(8) Ferric Pyrophosphate Content

A sample was strongly heated, and right away about 0.3 g of the sample where weighed precisely, were dissolved through addition of 20 mL of hydrochloric acid (1→2), and were transferred to a flask with ground-in stopper with 20 mL of water. Next, 3 g of potassium iodide were added, the whole was stoppered right away in an air-tight manner, and was allowed to stand in dark place for 15 minutes; thereafter, 100 mL of water were added, and iodine released through addition of a starch reagent solution was titrated using a 0.1 mol/L solution of sodium thiosulfate. The dropping amount was c (mL).

Separately, 20 mL of hydrochloric acid (1→2) and 20 mL of water were placed in a flask with ground-in stopper, then 3 g of potassium iodide were added, the flask was stoppered right away in an air-tight manner, and was allowed to stand for 15 minutes in a dark place. Thereafter, 100 mL of water were added, and iodine released through addition of a starch reagent solution was titrated using a 0.1 mol/L solution of sodium thiosulfate. This constituted a blank test. The ferric pyrophosphate content in 1 g of the powder containing ferric pyrophosphate was calculated from the titer, in accordance with the expression below. The dropping amount was d (mL).

Ferric pyrophosphate content (%)=((c−d)×0.01863/collected amount)×100

(9) Soluble Sodium Amount

Herein 5 g of a sample were precisely weighed in a beaker, and next there were added 100 mL of ultrapure water. The suspension thus prepared was heated for 15 minutes at 90° C. on a hot stirrer, and after heating was over the suspension was cooled in a water bath. Next, the suspension was transferred to a volumetric flask, was accurately brought to 100 mL with ultrapure water, the prepared suspension was centrifuged for 20 minutes in a centrifuge, and the resulting supernatant was retrieved. The supernatant was used to measure a sodium dissolving amount (e %), in accordance with the preparation method and measurement method of the standard solutions in (3) of Test example 1. The dissolving amount from 1 g in 1 mL of water was calculated on the basis of the expression below.

Soluble sodium amount (mg/mL)=(5×e/100)/100×1000

TABLE 1

| Test Item | | Sample 1 | Sample 2 | Sample 3 | Sample 4 | Sample 5 |
| --- | --- | --- | --- | --- | --- | --- |
| (Fe + Na)/P | — | 0.90 | 0.99 | 0.85 | 0.82 | 0.91 |
| b value in CIE LAB color system | — | 11.5 | 15.2 | 10.2 | 8.1 | 11.8 |
| Na content | % | 2.3 | 3.3 | 1.4 | 1.0 | 0.7 |
| Mode diameter (pore diameter of the maximum frequency) | nm | 159 | 137 | 242 | 321 | 231 |
| Specific surface area | m$^2$/g | 29.5 | 38.5 | 22.0 | 18.8 | 19.0 |
| Ferric pyrophosphate content | % | 95.7 | 95.1 | 97.3 | 98.4 | 99.4 |
| Soluble sodium amount | mg/mL | 0.16 | 0.20 | 0.11 | 0.03 | 0.00 |

TABLE 2

| Test Item | | Comparative sample 1 | Comparative sample 2 | Comparative sample 3 |
| --- | --- | --- | --- | --- |
| (Fe + Na)/P | — | 0.73 | 0.79 | 1.07 |
| b value in CIE LAB color system | — | 6.2 | 7.2 | 17.4 |
| Na content | % | 0.8 | 1.3 | 4.7 |
| Mode diameter (pore diameter of the maximum frequency) | nm | 605 | 559 | 145 |
| Specific surface area | m$^2$/g | 11.2 | 12.4 | 31.8 |
| Ferric pyrophosphate content | % | 97.9 | 96.3 | 96.3 |
| Soluble sodium amount | mg/mL | 0.02 | 0.15 | 0.16 |

Test Example 2

The degree of iron dissolution in each sample was evaluated. A dissolution test was performed in accordance with test conditions such as those given in Table 3. The measurements and the like were carried out in accordance with the methods described below.

TABLE 3

| | |
| --- | --- |
| Sample quantity | 200 mg/vessel |
| Apparatus | SR8 PLUS-8S (Hanson Research, USA) |
| Method | Paddle method |
| Test solution amount | 900 mL |
| Test solution temperature | 37° C. ± 0.5° C. |
| Rotational speed | 100 rpm |
| Test solution | First Fluid for dissolution test (pH 1.2) (Kanto Chemical Co., Inc.) Diluted McIlvaine Buffer Solution (pH 3.0) (Kanto Chemical Co., Inc.) |
| Collection time | 60 minutes after test |

<Preparation of a Sample Solution>

Herein 4 mL of a dissolution test collection solution, 1 mL of dilute nitric acid and 1 mL of an yttrium standard solution (100 ppm) were accurately measured in a volumetric flask, and were accurately brought to 20 mL with ultrapure water, to yield a sample solution.

<Preparation of Standard Solutions>

Iron standard solution (10 ppm):

Herein 5 mL of an iron standard solution (100 ppm) for atomic absorption analysis and 1 mL of dilute nitric acid were accurately measured in a volumetric flask, and ultrapure water was added to up to 50 mL.

Iron standard solution (1 ppm):

Herein 5 mL of the prepared standard solution (10 ppm) and 1 mL of dilute nitric acid were accurately measured in a volumetric flask, and ultrapure water was added to up to 50 mL.

Standard solution (a) (blank):

Herein 1 mL of an yttrium standard solution (100 ppm) and 1 mL of dilute nitric acid were accurately measured in a volumetric flask, and ultrapure water was added to up to 20 mL.

Standard solution (b) (Fe: 0.1 ppm):

Herein 1 mL of an yttrium standard solution (100 ppm) for atomic absorption analysis, 1 mL of dilute nitric acid, and 2 mL of an iron standard solution (1 ppm) were accurately measured in a volumetric flask, and ultrapure water was added to up to 20 mL.

Standard solution (c) (Fe: 0.5 ppm):

Standard solution (c) was prepared in the same way as standard solution (b), but herein there was accurately measured 1 mL of an iron standard solution (10 ppm) as the standard solution.

Standard solution (d) (Fe: 1 ppm):
Standard solution (d) was prepared in the same way as standard solution (b), but herein there were accurately measured 2 mL of an iron standard solution (10 ppm) as the standard solution.
Standard solution (e) (Fe: 5 ppm):
Standard solution (e) was prepared in the same way as standard solution (b), but herein there was accurately measured 1 mL of an iron standard solution (100 ppm) for atomic absorption analysis, as the standard solution.
Standard solution (f) (Fe: 15 ppm):
Standard solution (f) was prepared in the same way as standard solution (b), but herein there were accurately measured 3 mL of an iron standard solution (100 ppm) for atomic absorption analysis, as the standard solution.
<Measuring Method>
Inductively coupled plasma emission spectroscopy (ICP); calibration curve method
Detection wavelength: 259.941 nm
The intensities of standard solutions (a), (b), (c), (d), (e) and (f) were measured sequentially, to create a calibration curve. Next, the intensity of each sample solution was measured, the obtained intensity was converted to iron concentration in the measurement solution, and dissolving rates were calculated according to Expression 4 below. Table 4 shows the results for First Fluid for dissolution test (pH 1.2) of a dissolving test solution and the results of diluted McIlvaine Buffer Solution (pH 3.0).

$$\text{Dissolving rate (\%)} = ((f \times 20/4)/(\text{test charge amount (mg)} \times (\text{ferric pyrophosphate content}/100 \times 4 \times 55.85/745.22)/0.9) \times 100 \quad \text{(Expression 4)}$$

(where f=iron concentration (ppm) in the measurement solution)
ICP: SPECTRO ARCOS (by SII NanoTechnology Inc.)
Iron standard solution for atomic absorption analysis: Wako Pure Chemical Industries, Ltd.

It has been reported that iron is generally absorbed through the duodenum in an ionic state, and that dissolving of iron ions in the stomach gives rise to a drop in absorption amounts. In the present invention, therefore, the iron absorption rate (%) was checked as defined by Expression 5 below. The results are given in Table 4.

$$\text{Iron absorption rate (\%)} = (100 - \text{dissolving rate after 60 minutes at pH1.2}) \times \text{dissolving rate after 60 minutes at pH3.0}/100 \quad \text{(Expression 5)}.$$

TABLE 4

| Item | Dissolving rate (%) pH 1.2 | pH 3.0 | Iron absorption rate (%) |
|---|---|---|---|
| Sample 1 | 27.1 | 84.4 | 62 |
| Sample 2 | 40.4 | 94.8 | 57 |
| Sample 3 | 18.4 | 63.6 | 52 |
| Sample 4 | 20.6 | 62.7 | 50 |
| Sample 5 | 26.4 | 71.4 | 53 |
| Comparative sample 1 | 14.2 | 33.9 | 29 |
| Comparative sample 2 | 40.4 | 55.6 | 33 |
| Comparative sample 3 | 41.2 | 76.7 | 45 |

As the results of Table 4 reveal, the iron absorption rate in the comparative examples (Comparative samples 1 to 3) is 45% or lower. In the product of the present invention (Samples 1 to 5), by contrast, dissolving of iron at pH 1.2 is reduced, but a high dissolving rate is brought out at pH 3.0, and an iron absorption rate of 50% or higher is achieved as a result. That is, such a specific effect can be elicited in a case where the (Fe+Na)/P molar ratio in the ferric pyrophosphate-containing powder is controlled within a prescribed range. In the product of the present invention, thus, dissolving at pH 1.2 is decreased while dissolving at pH 3.0 is increased. As a result, it becomes possible to decrease dissolving of iron in the oral cavity and in the stomach while allowing iron to dissolve effectively at the duodenum, which can be expected to obtain high iron bioabsorbability.

Test Example 3

Iron absorbability was evaluated in an animal test, using Sample 5 and Comparative sample 2. Herein five rats of one group of four-week-old SD male rats were fed for two weeks with a low-Fe feed (AIN-93G base) powder feed (by CLEA Japan, Inc.), to elicit an iron deficiency state. After two weeks of feeding with the low-Fe feed (AIN-93G base) powder feed, blood was collected from the subclavian vein under anesthesia, and the serum was separated, after which there were measured serum iron concentration (serum iron), total iron binding capacity (TIBC), and iron saturation rate (TSAT) as an indicator for peripheral blood. Hemoglobin concentration (Hb) in blood was also measured. The results were serum iron 32.6 µg/dL, TIBC 749.5 µg/dL, Hb 9.0 g/dL, TSAT 4.4% and Hb 9.0 g/dL, which revealed that the rats were iron deficient. Thereafter, Sample 5 or Sample 7 was mixed into the low-Fe feed (AIN-93G base) powder feed, to yield an equivalent of 300 mg iron/kg per rat, and this mixed feed was fed ad libitum for 7 days; thereafter, blood was collected from the subclavian vein, under anesthesia, after 3 days and 7 days had elapsed. The serum in the collected blood was separated, and thereafter serum iron and serum TIBC were measured. Blood Hb was likewise measured. The results are given in Table 5 and Table 6.

TABLE 5

| | Sample 5 | | Sample 7 | |
|---|---|---|---|---|
| Item | 3 days | 7 days | 3 days | 7 days |
| Hb (g/dL) | 9.9 | 12.7 | 9.6 | 12.6 |

TABLE 6

| | Sample 5 | | Comparative sample 2 | |
|---|---|---|---|---|
| Item | 3 days | 7 days | 3 days | 7 days |
| Serum iron (µg/dL) | 322.0 | 277.0 | 549.2 | 368.6 |
| TIBC (µg/dL) | 604.0 | 517.2 | 630.0 | 498.6 |
| TSAT (%) | 54.8 | 53.1 | 87.0 | 73.7 |

It is clear from the results of Table 5 that Sample 5 is comparable or superior to Comparative sample 2. As the results of Table 6 reveal, Sample 5 exhibits a lower TSAT than that of Comparative sample 2. This is deemed to arise from the fact that the absorption rate of iron in Sample 5 is higher than that of Comparative sample 2, the absorbed iron is used for synthesis in the hematopoietic system, the period until the steady state is reached becomes shorter, and thus the recovery time from an anemic state is likewise shortened. The product of the present invention can accordingly be expected to result not only in a high iron absorption amount but also in a high iron absorption rate.

INDUSTRIAL APPLICABILITY

High iron absorbability is achieved by the powder of the present invention, and hence it becomes possible to simplify the formulation of various preparations or agents, to reduce use amounts, and to reduce dosages in patients with iron deficiency. By using the powder of the present invention, moreover, it becomes possible to provide a foodstuff, pharmaceutical, cosmetic or the like in which the problems of palatability and stomach upsetting are alleviated or averted.

The invention claimed is:

1. A composite powder containing ferric pyrophosphate and a sodium component, wherein
   (1) the content of ferric pyrophosphate is 95 wt % or higher, and
   (2) a (Fe+Na)/P molar ratio is 0.82 to 1.0.

2. The composite powder according to claim 1, having a mode diameter as a pore diameter of the maximum frequency of 500 nm or less.

3. The composite powder according to claim 1, having a b value as a hue of 16 or smaller in the CIE LAB color system.

4. The composite powder according to claim 1, comprising 0.5 to 4.5 wt % of Na.

5. The composite powder according to claim 1, having a specific surface area of 15 m2/g or higher.

6. An iron supplement foodstuff, comprising the composite powder according to claim 1.

7. A pharmaceutical composition, comprising the composite powder according to claim 1.

8. A method for producing a composite powder containing ferric pyrophosphate and a sodium component, the method comprising:
   a step of preparing an aqueous slurry that contains a reaction product obtained by reacting a water-soluble ferric salt, a pyrophosphate and a carbonate in an aqueous solvent, the aqueous slurry being prepared through addition and mixing such that a (Fe+Na)/F molar ratio of the reaction product is 0.82 to 1.0.

9. The production method according to claim 8, wherein the carbonate is sodium carbonate.

10. The production method according to claim 8, wherein a water-soluble iron salt, a pyrophosphate and a carbonate, which are prepared in the form of aqueous solutions beforehand, are added and mixed such that a molar ratio (Fe+Na)/P of the starting material charge is 2.7 to 3.1.

* * * * *